(12) United States Patent
Takata et al.

(10) Patent No.: US 7,492,459 B2
(45) Date of Patent: Feb. 17, 2009

(54) OPTICAL DROPLET SENSOR AND METHOD

(75) Inventors: Hiroshi Takata, Tokyo (JP); Kiyomitsu Ishikawa, Tokyo (JP); Yorimi Yokoyama, Tokyo (JP)

(73) Assignee: Stanley Electric Co., Ltd., Tokyo (JP)

( * ) Notice: Subject to any disclaimer, the term of this patent is extended or adjusted under 35 U.S.C. 154(b) by 82 days.

(21) Appl. No.: 11/276,837

(22) Filed: Mar. 16, 2006

(65) Prior Publication Data

US 2006/0215164 A1 Sep. 28, 2006

(30) Foreign Application Priority Data

Mar. 22, 2005 (JP) ............................. 2005-082153

(51) Int. Cl.
*G01N 21/55* (2006.01)
(52) U.S. Cl. .................... 356/445; 356/448; 356/237.5; 250/227; 250/341.8; 250/574
(58) Field of Classification Search ................ 356/445, 356/448, 237.1–237.5; 250/227–227.25, 250/341.8, 574; 340/601–604
See application file for complete search history.

(56) References Cited

U.S. PATENT DOCUMENTS

| 5,661,303 A | * | 8/1997 | Teder ...................... 250/341.8 |
| 6,627,910 B2 | | 9/2003 | Ishino et al. |
| 6,855,947 B2 | * | 2/2005 | Graves et al. .......... 250/227.25 |

* cited by examiner

*Primary Examiner*—L. G Lauchman
*Assistant Examiner*—Iyabo S Alli
(74) *Attorney, Agent, or Firm*—Cermak Kenealy Vaidya & Nakajima LLP

(57) ABSTRACT

An optical droplet sensor can include a light emitter, a light receiver and a light guide, and can be adhered onto an inner surface of a windshield via a light transmissive adhesive layer. The light guide can include a light entry surface and a light exit surface formed of respective convex-shaped arbitrary curved surfaces, a light entry/exit surface formed of a flat plane, and a reflecting surface that can be made of a metal film. The light emitted from the light emitter is given an optimized light distribution at the light entry surface and introduced into the light guide. The light is then reflected from the metal film-applied reflecting surface toward an outer surface of the windshield. The light totally reflected at the outer surface returns to the light exit surface and is given an optimized light distribution at the light exit surface. The light is then externally transmitted/released from the light guide and collected on a light-receiving surface of the light receiver.

25 Claims, 4 Drawing Sheets

OPTICAL DROPLET SENSOR AND METHOD

This application claims the priority benefit under 35 U.S.C. §119 of Japanese Patent Application No. 2005-082153 filed on Mar. 22, 2005, which is hereby incorporated in its entirety by reference.

BACKGROUND

1. Field

The disclosed subject matter relates to an optical droplet sensor and method capable of optically detecting droplets attached to a surface of a light transmissive structure, for example, a windshield plate.

2. Description of the Related Art

An optical droplet sensor is conventionally installed on an inner surface of a windshield of a vehicle and detects droplets attached on an outer glass surface thereof for automatically operating wipers to ensure a fine view while driving in rain. An example of such an optical droplet sensor is described as follows.

This conventional sensor includes a beam transmitter 50 and a beam receiver 51 mounted on a printed circuit board 52 as shown in FIG. 6 such that respective optical axes in exit and entry directions cross each other. Two plane-convex lenses 53a, 53b are integrated through a coupling section 54 to form a prism lens 55, which is arranged such that optical axes of the plane-convex lenses 53a, 53b match the optical axes of the beam transmitter 50 and the beam receiver 51, respectively.

When the optical droplet sensor thus configured is installed on an inner surface 57 of a windshield glass 56, light emitted from the light emitter 50 is transformed into parallel light through the plane-convex lens 53a and introduced into the prism lens 55. The parallel light introduced into the prism lens 55 repeats reflections (total reflections) between an outer surface 58 of the windshield glass 56 and an outer circumferential surface 59 of the coupling section 54 and reaches the plane-convex lens 53b. The parallel light received at the plane-convex lens 53b is collected through the plane-convex lens 53b, then exits outward from the prism lens 55 and enters the beam receiver 51.

In general, the density of raindrops is lower at the beginning of rainfall. Even in such case, reliable detection of rainfall benefits from a wide raindrop detection region and an improvement in accuracy of raindrop detection. For that purpose, in the optical droplet sensor configured as described above, a device is applied to widen the raindrop detection region and to increase the number of reflections (total reflections) between the outer surface of the windshield glass and the outer circumferential surface of the coupling section in the prism lens. The device is directed to arrange both the beam transmitter and the beam receiver outside the prism lens. In this case, however, the shape/size of the raindrop sensor in the direction of the length disadvantageously becomes larger. In addition, the area of the raindrop detection region may still be insufficient, and thus it is difficult to perform high-accuracy droplet detection.

To address the above and other issues, another conventional optical droplet sensor can be used, which is configured as shown in FIG. 7. This sensor includes a beam transmitter 60 and a beam receiver 61 arranged in parallel and a prism lens 62 formed to be almost U-shaped in section. The sensor has opposite inner faces on arc-curved convex lenses 63a, 63b, which are formed by rotating arc shapes in section about the beam transmitter 60 and the beam receiver 61, respectively. The arc-curved convex lenses 63a, 63b have outer circumferential faces 64a, 64b, which are shaped to be parabolic.

When the optical droplet sensor thus configured is installed on an inner surface 66 of a windshield glass 65, light emitted from the light emitter 60 is transformed into parallel light through the arc-curved convex lens 63a and introduced into the prism lens 62. The parallel light introduced into the prism lens 62 travels toward the outer circumferential face 64a of the arc-curved convex lens 63a on the side close to the light emitter 60. It is then reflected (totally reflected) from the outer circumferential face 64a and travels toward an outer surface 67 of the windshield glass 65. The parallel light traveling toward the outer surface 67 of the windshield glass 65 is reflected (totally reflected) from the outer surface 67 of the windshield glass 65 and travels toward the outer circumferential face 64b of the arc-curved convex lens 63b on the side close to the light receiver 61. It is then reflected (totally reflected) from the outer circumferential face 64b and travels toward the arc-curved convex lens 63b on the side close to the light receiver 61. The parallel light received at the arc-curved convex lens 63b on the side close to the light receiver 61 is collected through the arc-curved convex lens 63b on the side close to the light receiver 61. It is then released outward from the prism lens 62 and enters the beam receiver 61 (for example, please see U.S. Pat. No. 6,627,910, which is hereby incorporated in its entirety by reference).

The optical droplet sensor thus configured has a narrowed interval between the beam transmitter and the beam receiver arranged in parallel to reduce the shape/size in the direction of the length. It has a function of receiving the light emitted from the beam transmitter and introduced into the prism lens and directing the light to the outer surface of the windshield glass. It also has a function of receiving the light reflected from the outer surface of the windshield glass and directing the light to the arc-curved convex lens on the side close to the light receiver. These functions are achieved by forming the respective outer circumferential faces of the arc-curved convex lenses as reflecting surfaces (total reflecting surfaces).

To make the outer circumferential face of the arc-curved convex lens function as the reflecting surface (total reflecting surface), the light emitted from the beam transmitter and introduced into the prism lens, and the normal to the outer circumferential face of the arc-curved convex lens are required to have an angle of intersection (an angle of incidence of light to the outer circumferential face of the arc-curved convex lens) larger than a critical angle. At the same time, the light reflected from the outer surface of the windshield glass, and the normal to the outer circumferential face of the arc-curved convex lens are required to have an angle of intersection (an angle of incidence of light to the outer circumferential face of the arc-curved convex lens) larger than a critical angle. Therefore, it is required to set a longer distance between each of the beam transmitter and the beam receiver and the outer circumferential face of the arc-curved convex lens in the direction almost normal to the windshield glass. As a result, the shape/size in the direction of the height of the raindrop sensor becomes larger.

SUMMARY

An optical droplet sensor can be configured to be capable of being downsized and have high flexibility of design and high detection accuracy.

In accordance with a first aspect, an optical droplet sensor can be installed on one surface of a light transmissive structure, such as a windshield plate, and operative to detect droplets attached on the other surface thereof. The optical droplet sensor can include a light emitter, a light receiver, and a light guide. The light guide can include a light entry surface for introducing light emitted from the light emitter into the light guide, a light exit surface having a convex shape protruding externally for emitting/releasing light guided through the light guide to a location external to the light guide, and a side reflector having a metal-containing film formed for directing light introduced into the light guide toward the light transmissive structure, or a secondary side reflector composed of a first side reflector having a metal-containing film formed for directing light introduced into the light guide toward the light transmissive structure and a second side reflector having a metal-containing film formed for directing light reflected from the light transmissive structure toward the light exit surface.

In a second aspect, the reflector surfaces of the light guide can have a shape selected from the group consisting of: a flat plane; an arbitrary curved convex shape; and an arbitrary curved concave shape.

In a third aspect, a flange can be provided at the outer rim of the reflector surface of the light guide such that the flange protrudes outward from the reflector surface.

The optical droplet sensor is installed on one surface of the light transmissive structure to detect droplets attached on another surface thereof. A light guide contained in the optical raindrop sensor can include a light entry surface formed of an arbitrary curved convex surface with an optimized light distribution characteristic for introducing the light emitted from the light emitter into the light guide. It also has a light exit surface that can be formed of an arbitrary curved convex surface with an optimized light distribution characteristic for releasing/emitting the light guided through the light guide outward from the light guide and focusing the light on the light receiver. Therefore, optimization of a droplet detection range on the light transmissive structure and enhanced efficiency of collection of light to the light receiver can improve the accuracy of detection of droplets.

The reflector surfaces can include a metal film-applied reflecting surface provided on the light guide for changing the direction of light traveling through the light guide. Accordingly, it is possible to prevent light from leaking outward from the light guide and reduce light not contributing to detection of droplets so as to promote effective utilization of light. Also from this point, the accuracy of detection of droplets can be improved. As the direction of traveling light can be changed at the reflecting surfaces, it is possible to relieve the constraints on positioning for the light emitter and the light receiver, enhance the flexibility of design, and downsize the sensor. In addition, forming the reflecting surface as an arbitrary curved surface controls the distribution characteristic of light in the light guide, and making the function of optimizing the distribution characteristics at other parts to be collected on the reflecting surface achieves a downsizing feature.

Further, a flange can be provided at the outer rim of a metal film that constitutes the reflecting surface such that the flange protrudes outward from the outer rim. As a result, when metal material is evaporated, metal particles are prevented from attaching on undesired parts of the light guide. Accordingly, a high-productivity manufacturing method can be applied to reduce the production cost.

DETAILED DESCRIPTION OF EXEMPLARY EMBODIMENTS

Figure 1:
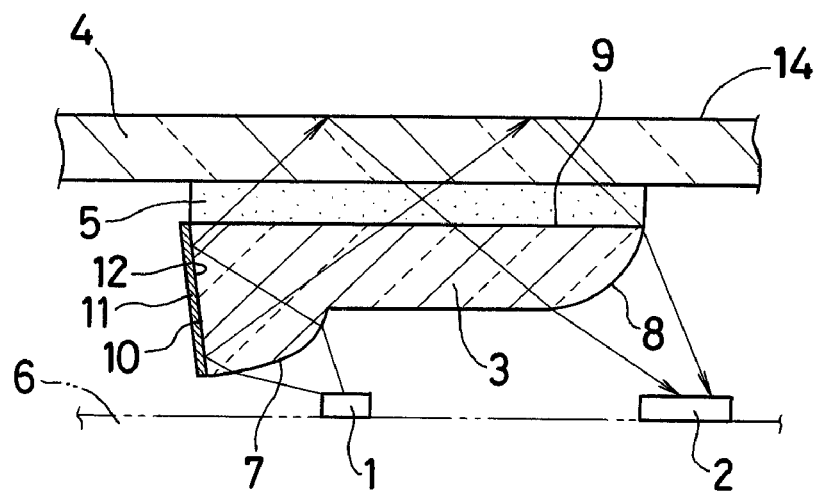
FIG. 1 is a cross-sectional view showing an exemplary embodiment of an optical droplet sensor that is made in accordance with principles of the disclosed subject matter, and installed on a windshield.

An optical droplet sensor capable of being downsized and having high flexibility of design and high accuracy of detection can be achieved as follows. A light guide contained in the optical raindrop sensor can include a light entry surface formed of an arbitrary curved convex surface with an optimized light distribution characteristic for introducing the light emitted from the light emitter into the light guide. A light exit surface can be formed of an arbitrary curved convex surface with an optimized light distribution characteristic for releasing/transmitting the light guided through the light guide outward from the light guide and focusing the light on the light receiver. Further, the sensor can include a reflecting surface, such as a metal film-applied reflecting surface, provided on the light guide for changing the direction of light traveling through the light guide.

Exemplary embodiments of the disclosed subject matter will now be described in detail with reference to FIGS. 1-5 (with the same reference numerals denoting the same or similar parts). The embodiments described below are examples of the disclosed subject matter and are given various technical features. However, the scope of the disclosed subject matter is not limited to these embodiments.

FIG. 1 is a cross-sectional view showing an example of an optical droplet sensor that is made in accordance with principles of the disclosed subject matter, and which is installed on one surface of a windshield which can be made from various materials, including glass, plastic, other resins, etc. The optical droplet sensor can include a light emitter 1, a light receiver 2, and a light guide 3, and can be adhered onto one surface of a windshield 4 via a light transmissive adhesive layer 5.

The light emitter 1 and the light receiver 2 of the optical droplet sensor can be mounted on a printed circuit board 6 and aligned at a certain interval. The light-emitting direction of the light emitter 1 and the light-receiving direction of the light receiver 2 are pointed in opposite directions. The light emitter 1 of this embodiment is a semiconductor light-emitting device, that is, a light-emitting diode (LED), which may be an LED bare chip or an LED device including an LED bare chip sealed in a package. The wavelength of the LED is not particularly limited, but can be within a range between the UV region and the infrared region. To ensure high accuracy of detection, the use of light with such a wavelength can enhance the sensitivity of the light receiver 2 for receiving light.

On the other hand, the light receiver 2 can act as a semiconductor photoreceptor, that is, a PIN photodiode, a photodiode, a phototransistor, etc., which may be a respective bare chip or a photoreceptor device including a bare chip sealed in a package.

The light guide 3 can be composed of a light transmissive resin, glass, other plastics, etc., and arranged in the light-emitting direction of the light emitter 1 and the light-receiving direction of the light receiver 2 (above the light emitter and the light receiver). The light guide can include the following surfaces: a light entry surface 7 that is operative to introduce much of the light emitted from the light emitter 1 into the light guide 3; a light exit surface 8 that is operative to transmit/release much of the light guided through the light guide 3 outward from the light guide 3; a light entry/exit surface 9 that serves as both a light entry surface and a light exit surface. The light entry surface of the light entry/exit surface can be operative to transmit/release light from the light guide 3 toward the windshield 4. The light exit surface of the light entry/exit surface can be operative to introduce part of the light transmitted/released toward the windshield 4 and reflected (totally reflected) from the windshield 4 into the light guide 3 again. The light entry surface 7 and the light exit surface 8 can be formed of convex-shaped arbitrary curved surfaces, and the light entry/exit surface 9 formed of a flat plane. A light-transmissive adhesive layer can be provided on the light entry/exit surface 9 to install the optical droplet sensor on the windshield via the adhesive layer.

The light guide 3 has a side 10 close to the light emitter 1. The side can be formed of an almost flat plane, on part or the entire of which, a metal film 11, such as Al or Ag film(s) is/are formed through a process of evaporation, and can thus serve as a reflecting surface 12.

During formation of the metal-evaporated film on the surface of the light guide, because the light guide has evaporation-inhibited regions such as the light entry surface, the light exit surface, and the light entry/exit surface, it is possible for the metal-evaporated film to be located only on the desired part in the surface of the light guide. In this case, to form the metal-evaporated film only on the desired part, a process of evaporation is applied after masking the parts that desire no metal-evaporated film formed on the surface of the light guide.

Figure 2:
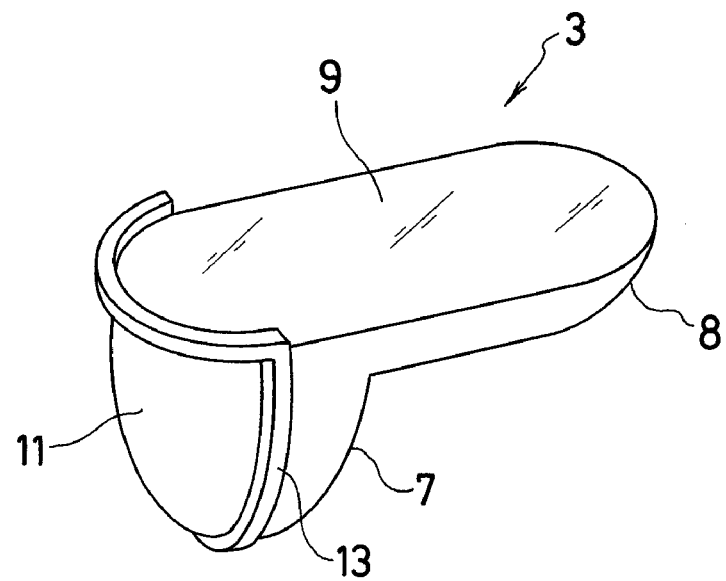
FIG. 2 is a perspective view of a light guide of the optical droplet sensor of FIG. 1.

This method includes masking in the manufacturing processes, and therefore invites a reduction in production yield. In addition, the method is sometimes inefficient because the light guide can have a sophisticated shape and small size and, accordingly, the work of masking becomes complicated. However, it is possible to form the metal-evaporated film only on the desired part in the surface of the light guide efficiently and without masking. For that purpose, when an evaporating method is applied to form a metal film 11 on the surface of the light guide 3, a flange 13 can be provided at the outer rim of the surface such that the flange protrudes outward from the outer rim, as shown in FIG. 2.

The light guide is located in an evaporator for evaporation such that an evaporation-targeted surface of the light guide is opposed to a metal evaporation source. In this case, metal evaporation particles vaporized from the evaporation source and diffused deposit on the evaporation-targeted surface of the light guide and the flange to form an evaporated film. As for other surfaces that are located within the region, the vaporized metal evaporation particles can be prevented from diffusing thereon by the flange, i.e., substantially little or no metal particle reach certain portions of the surface of the light guide, and little or no evaporated film is formed thereon.

The optical raindrop sensor 3, the windshield 4, and the adhesive layer 5 form an optical system, which is described below. The light source or the light emitter 1 (for example, an LED) emits light, much of which reaches the light entry surface 7 of the light guide 3. The light emitted from the LED has a broad directionality. Accordingly, the light entry surface 7 is formed of an arbitrary curved convex surface such that the light distribution characteristic is optimized for introducing light into the light guide 3. In this case, the arbitrary curved surface can be designed in consideration of the directionality of the light emitted from the LED, the distance from the LED to the arbitrary curved surface, the distribution characteristic of light introduced into the light guide 3, the refractive index of light transmissive material contained in the light guide 3, and other factors, to form an optimal curved surface.

The light emitted from the LED and introduced through the light entry surface 7 of the arbitrary curved surface into the light guide 3 (and having an optimized light distribution), travels toward the reflecting surface 12 that can be made of the metal film 11 formed on the side 10 of the light guide 3. It is then reflected from the reflecting surface 12 and travels toward the windshield 4. The light traveling toward the windshield 4 is then transmitted/released from the light guide 3 through the light exit surface 9 of the light guide 3. Thereafter, it passes through the adhesive layer 5 and reaches the outer surface 14 of the windshield 4.

The position and range of droplet detection can be controlled by setting the distribution characteristic of light introduced into the light guide, the distance of the reflecting surface of the light guide from the light entry surface, the slanting angle of the reflecting surface of the light guide to the light entry surface, and other characteristics.

Figure 3:
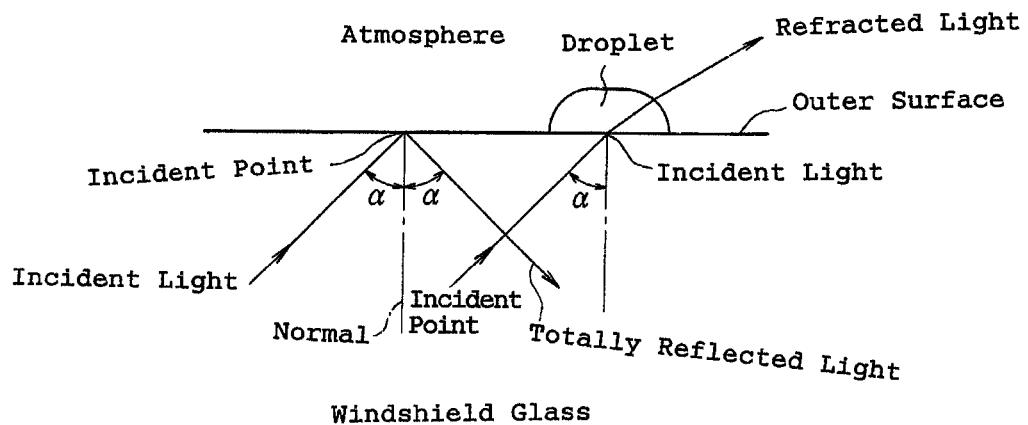
FIG. 3 is an illustrative view of the principle of droplet detection at the optical droplet sensor according to an embodiment made in accordance with principles of the disclosed subject matter.

In this case, as shown in FIG. 3, consideration may be given to the case where a droplet is present on a light incident point on the outer surface of the windshield and the case where no droplet is present (the atmosphere is present). When no droplet is present and an interface is formed between the atmosphere and the outer surface of the windshield, the incident angle, $\alpha$, of light to the outer surface of the windshield glass may be larger than a critical angle. In this case, the light is reflected from the outer surface of the windshield glass at an angle of $\alpha$ equal to the incident angle, $\alpha$, and returns into the windshield glass.

On the other hand, when a droplet is present, as the droplet has a larger refractive index than that of the atmosphere, the critical angle becomes larger. Therefore, the light received on the outer surface of the windshield at the angle of $\alpha$ smaller than the critical angle is refracted from the outer surface of the windshield and transmitted/released through the droplet into the atmosphere.

Thus, in the optical droplet sensor, the windshield and the substance that forms the interface with the outer surface of the windshield have a difference in refractive index ratio, which changes the critical angle for total reflection. The light incident to the interface at the same incident angle is totally reflected or refracted depending on the substances that form the interface. This phenomenon is utilized in the optical droplet sensor.

The light reflected at the outer surface 14 of the windshield 4 travels toward the light exit surface 8 of the light guide 3, passes through the adhesive layer 5, and reaches the light exit surface 8. In this case, the arbitrary curved surface is designed in consideration of: the distribution characteristic of light reflected from the outer surface 14 of the windshield 4 and guided through the light guide 3 to the arbitrary curved surface; the positional relation between the arbitrary curved surface and the light receiver; the refractive index of light transmissive material contained in the light guide 3; and other factors, to form an optimal curved surface such that the light transmitted/released from the light exit surface 8 is efficiently collected on the light receiver.

Much of the light transmitted/released from the light exit surface 8 is collected on the light receiver 2, then converted into an electric signal at the light receiver 2 and sent therefrom to a detection processor circuit (not shown). The presence/absence of droplets and the density of attached droplets may be detected as follows. If an amount of light received at the light receiver is lower than the amount of light received at the light receiver when no droplet is present, it is determined that a droplet is attached to the outer surface 14 of the windshield 4. The density of droplets is proportional to the reduced amount relative to the amount of light received at the light receiver when no droplet is present.

Therefore, smooth and accurate detection of the beginning of rainfall is enhanced by setting the detection range to be wider. Widening the detection range, however, can result in a wider dispersion of a certain amount of light emitted from the light emitter (widening of the light distribution). In such a case, the luminous flux density in the unit area of the detection range lowers, and a difference in the amount of light received at the light receiver becomes extremely small. As a result, the detection accuracy can deteriorate and cause a result opposed to the original purpose.

The measures effective for preventing such a contrary phenomenon include using a brighter light source to increase the amount of light, and reducing light that does not contribute to detection among the light emitted from the light source to utilize the light efficiently. For that reason, the shapes of the arbitrary curved surfaces of the light entry surface and the light exit surface of the light guide, the positional relation between the light emitter and the light entry surface, and the positional relation between the light receiver and the light entry surface can aid in offsetting this contrary phenomenon. In addition, the metal film-applied reflecting surface can be formed on the side of the light guide such that the light emitted from the light emitter and introduced into the light guide is reflected at the metal film-applied reflecting surface toward the windshield. These are effective approaches.

In particular, the metal reflecting surface reflects all or substantially all of the light received at the reflecting surface independent of the angle of incidence. Accordingly, it is possible to prevent light from externally leaking from the light guide at some midpoint in the optical path and to use the light efficiently in detection of droplets. Thus, the optical droplet sensor can be made highly reliable. In addition, it is not required to consider the angle of incidence to the reflecting surface. Accordingly, it is possible to reflect light even when the angle of incidence is smaller than the critical angle where the metal reflecting surface is not present. This is effective to enhance the flexibility of optical design and to downsize the sensor.

Figure 4:
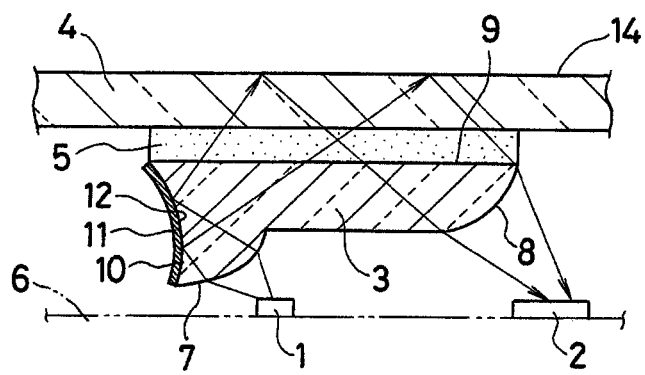
FIG. 4 is a cross-sectional view showing another exemplary embodiment of an optical droplet sensor that is made in accordance with principles of the disclosed subject matter, and installed on a windshield.

FIG. 4 is a cross-sectional view showing another embodiment of the optical droplet sensor which is installed on one surface of a windshield. This example is similar to the embodiment of FIG. 1 except that the shape of the side 10 of the light guide 3 is formed of a curved surface, on which the reflecting surface 12 made of the metal film 11 is formed. Accordingly, a description of similar parts is omitted.

This example is configured to freely determine the position and range of droplet detection and further downsize the sensor when the reflecting surface 12 is formed of a desired curved surface. The metal film 11 formed through an evaporating method can include an outer rim. A flange can be provided at the outer rim such that the flange protrudes outward from the outer rim. This is effective to prevent metal particles from attaching to undesired parts of the light guide 3 during evaporation.

Figure 5A:
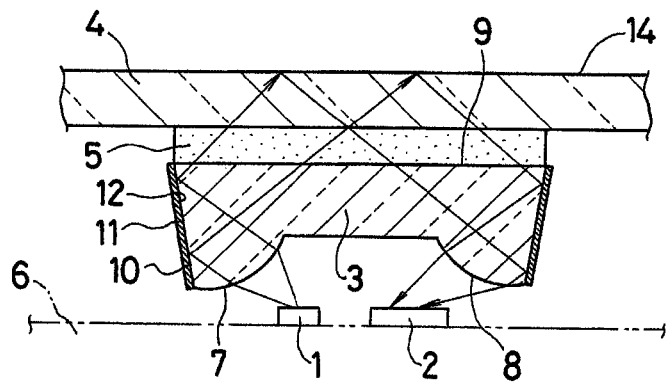
FIGS. 5A and B are cross-sectional views showing additional exemplary embodiments of an optical droplet sensor that is made in accordance with principles of the disclosed subject matter, and installed on a windshield.
Figure 5:
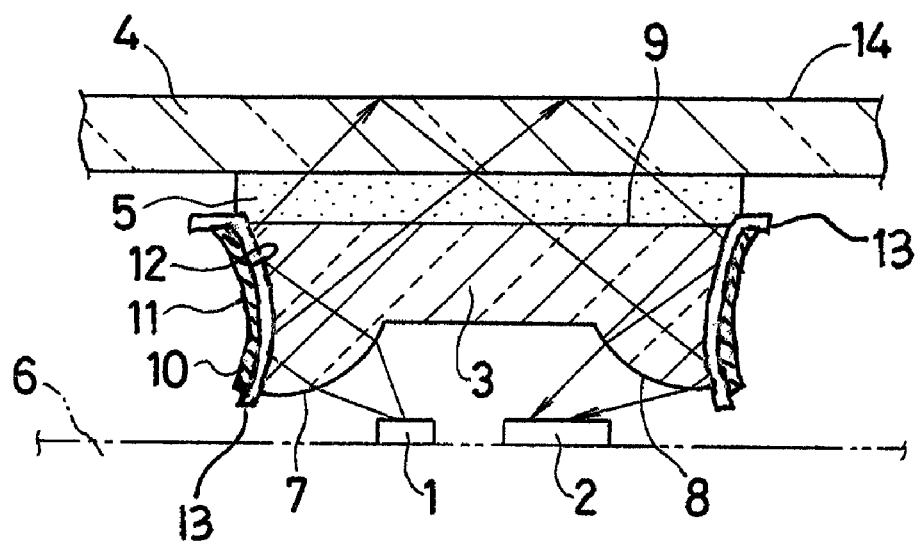
Figure 6:
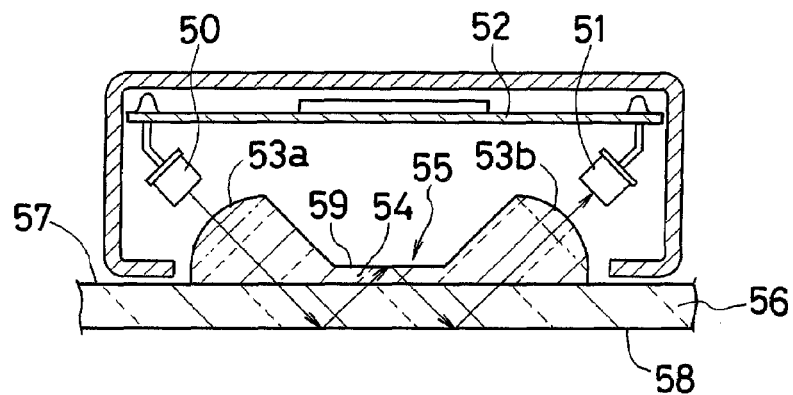
FIG. 6 is a cross-sectional view showing a conventional art optical droplet sensor, which is installed on a windshield.
Figure 7:
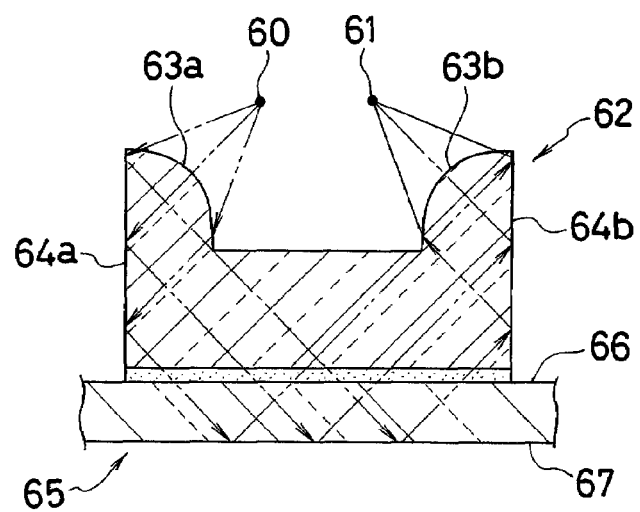
FIG. 7 is a cross-sectional view showing another conventional art optical droplet sensor, which is installed on a windshield.

FIG. 5A is a cross-sectional view showing another embodiment of an optical droplet sensor installed on a surface of a windshield. This example is similar to the example of FIG. 1 except that both sides of the light guide close to the light emitter and the light receiver are formed of flat planes and the metal film-applied reflecting surface is formed on the flat planes. Accordingly, a description of similar parts is omitted.

In this example, both sides 10 of the light guide 3 close to the light emitter 1 and the light receiver 2 are formed of flat planes, and the reflecting surface 12 made of the metal film 11 is formed on the flat planes. Thus, the light received at the reflecting surfaces close to the light emitter 1 and the light receiver 2 can be reflected independent of the angle of incidence, respectively. Accordingly, it is possible to prevent light from externally leaking from the light guide at some midpoint in the optical path, and it is possible to use the light efficiently in detection of droplets. Thus, the optical droplet sensor can be made highly reliable. In addition, it is not required to consider the angle of incidence to the reflecting surface. Accordingly, it is possible to reflect light even when the angle of incidence is smaller than the critical angle where the metal reflecting surface is not present. This is effective to enhance the flexibility of optical design and further downsize the sensor.

FIG. 5B is a cross-sectional view showing another embodiment of an optical droplet sensor installed on a surface of a windshield. This example is similar to the example of FIG. 5A, except that both sides of the light guide include a reflector that has an arbitrary curved shape, for directing light transmitted and released from the light guide in a specific manner.

In the light guide contained in another embodiment of an optical droplet sensor, the metal film-applied reflecting surface can be formed close to the light emitter and/or the light receiver. In addition, the side of the light guide having the metal film formed thereon can be shaped in the form of a flat plane or a curved surface. In the metal film-applied reflecting surface, a flange can be provided at the outer rim of the reflecting surface of the light guide such that the flange protrudes outward from the reflecting surface.

Even if the light guide is configured in this manner, the positions of the light emitter and the light receiver can be interchanged without loss of function. In other words, interchanging the positions of the light emitter and the light receiver causes little or no change in the product's efficiency or operation.

The optical droplet sensor and method can be used to detect various types of droplets, including rain, fog, mist, ice, snow, road spray, dirt, etc.

While there has been described what are at present considered to be exemplary embodiments of the disclosed subject matter, it will be understood that various modifications may be made thereto, and it is intended that the appended claims cover all such modifications as fall within the true spirit and scope of the invention.

What is claimed is:

1. An optical droplet sensor configured for installation on a surface of a light transmissive structure, and operative to detect droplets attached on another surface of the light transmissive structure, the optical droplet sensor comprising:

a light emitter;

a light receiver; and a light guide located adjacent the light emitter and light receiver, the light guide including, a light entry surface having an externally protruding convex shape configured to receive light emitted from the light emitter into the light guide, a light exit surface having an externally protruding convex shape configured to release light guided through the light guide to external, and at least one of a primary side reflector having a metal-containing film and configured to direct light introduced into the light guide toward the light transmissive structure, wherein, light reflected from the transmissive structure is directed toward the light exit surface, and a secondary side reflector composed of a first side reflector having a metal-containing film and configured to direct light introduced into the light guide toward the light transmissive structure and a second side reflector having a metal-containing film and configured to direct light reflected from the light transmissive structure toward the light exit surface, wherein the light guide comprises a single unitary structure.

2. The optical droplet sensor according to claim 1, wherein the primary side reflector of the light guide is shaped as a flat plane.

3. The optical droplet sensor according to claim 1, further comprising:

a flange located at an outer periphery of the primary side reflector wherein the flange protrudes outward from the primary side reflector.

4. The optical droplet sensor according to claim 1, further comprising:

a flange located at an outer periphery of the first side reflector wherein the flange protrudes outward from the first side reflector.

5. The optical droplet sensor according to claim 1, further comprising:

a flange located at an outer periphery of the second side reflector wherein the flange protrudes outward from the second side reflector.

6. The optical droplet sensor according to claim 2, further comprising:

a flange located at an outer periphery of the primary side reflector wherein the flange protrudes outward from the primary side reflector.

7. The optical droplet sensor according to claim 1, wherein the primary side reflector of the light guide has an arbitrary curved convex shape.

8. The optical droplet sensor according to claim 1, wherein the first side reflector of the light guide is shaped as a flat plane.

9. The optical droplet sensor according to claim 8, further comprising:

a flange located at an outer periphery of the first side reflector wherein the flange protrudes outward from the first side reflector.

10. The optical droplet sensor according to claim 1, wherein the first side reflector of the light guide has an arbitrary curved convex shape.

11. The optical droplet sensor according to claim 10, further comprising:

a flange located at an outer periphery of the first side reflector wherein the flange protrudes outward from the first side reflector.

12. The optical droplet sensor according to claim 1, wherein the second side reflector of the light guide is shaped as a flat plane.

13. The optical droplet sensor according to claim 1, wherein the second side reflector of the light guide has an arbitrary curved convex shape.

14. An optical droplet sensor configured for installation on a surface of a light transmissive structure, and operative to detect droplets attached on another surface of the light transmissive structure, the optical droplet sensor comprising:

a light emitter;

a light receiver; and a light guide located adjacent the light emitter and light receiver, the light guide including, a light entry surface facing the light emitter and having an externally protruding convex shape configured to receive light emitted from the light emitter into the light guide, a light exit surface having a convex shape configured to externally transmit light guided through the light guide, and at least one of, a primary side reflector having a reflective surface configured to direct light introduced into the light guide toward the light transmissive structure, wherein, light reflected from the light transmissive structure is directed toward the light exit surface, and a secondary side reflector including a first side reflector having a reflecting surface configured to direct light introduced into the light guide toward the light transmissive structure and a second side reflector having a reflecting surface configured to direct light reflected from the light transmissive structure toward the light exit surface.

15. The optical droplet sensor according to claim 14, wherein the primary side reflector of the light guide is shaped as a flat plane.

16. The optical droplet sensor according to claim 14, further comprising:

a flange located at an outer periphery of the primary side reflector wherein the flange protrudes outward from the primary side reflector.

17. The optical droplet sensor according to claim 14, further comprising:

a flange located at an outer periphery of the second side reflector wherein the flange protrudes outward from the second side reflector.

18. The optical droplet sensor according to claim 14, wherein the first side reflector of the light guide is shaped as a flat plane.

19. The optical droplet sensor according to claim 14, wherein the first side reflector of the light guide has an arbitrary curved convex shape.

20. The optical droplet sensor according to claim 14, wherein the primary side reflector of the light guide has an arbitrary curved convex shape.

21. The optical droplet sensor according to claim 1, wherein the primary side reflector of the light guide has an arbitrary curved concave shape.

22. The optical droplet sensor according to claim 1, wherein the first side reflector of the light guide has an arbitrary curved concave shape.

23. The optical droplet sensor according to claim 1, wherein the second side reflector of the light guide has an arbitrary curved concave shape.

24. The optical droplet sensor according to claim 14, wherein the first side reflector of the light guide has an arbitrary curved concave shape.

25. The optical droplet sensor according to claim 14, wherein the primary side reflector of the light guide has an arbitrary curved concave shape.

* * * * *